(12) United States Patent
Iddan

(10) Patent No.: US 6,939,290 B2
(45) Date of Patent: Sep. 6, 2005

(54) SELF PROPELLED DEVICE HAVING A MAGNETOHYDRODYNAMIC PROPULSION SYSTEM

(75) Inventor: Gavriel J. Iddan, Haifa (IL)

(73) Assignee: Given Imaging Ltd, Yoqneam (IL)

(*) Notice: Subject to any disclaimer, the term of this patent is extended or adjusted under 35 U.S.C. 154(b) by 0 days.

(21) Appl. No.: 10/361,861

(22) Filed: Feb. 11, 2003

(65) Prior Publication Data

US 2003/0214580 A1 Nov. 20, 2003

Related U.S. Application Data

(60) Provisional application No. 60/354,926, filed on Feb. 11, 2002.

(51) Int. Cl.[7] .................................................. A61B 1/00
(52) U.S. Cl. ..................................................... 600/109
(58) Field of Search ................................. 600/301, 309, 600/371, 407, 410, 419, 424, 448, 459, 462, 485, 486, 505, 109, 114; 440/6

(56) References Cited

U.S. PATENT DOCUMENTS

| | | |
|---|---|---|
| 3,322,374 A | 5/1967 | King, Jr. |
| 3,683,389 A | 8/1972 | Hollis |
| 3,971,362 A | 7/1976 | Pope et al. |
| 4,278,077 A | 7/1981 | Mizumoto |
| 4,689,621 A | 8/1987 | Kleinberg |
| 4,741,327 A | 5/1988 | Yabe |
| 4,844,076 A | 7/1989 | Lesho et al. |
| 5,279,607 A | 1/1994 | Schentag et al. |
| 5,398,670 A | 3/1995 | Ortiz et al. |
| 5,435,761 A * | 7/1995 | Shimamune et al. ........... 440/6 |
| 5,604,531 A | 2/1997 | Iddan et al. |
| 5,643,175 A | 7/1997 | Adair |
| 5,662,587 A | 9/1997 | Grundfest et al. |
| 5,819,736 A | 10/1998 | Avny et al. |
| 6,240,312 B1 | 5/2001 | Alfano et al. |
| 6,632,175 B1 | 10/2003 | Marshall |
| 2001/0017649 A1 | 8/2001 | Yaron |
| 2001/0051766 A1 | 12/2001 | Gazdzinski |
| 2002/0103417 A1 | 8/2002 | Gazdzinski |
| 2002/0173718 A1 | 11/2002 | Frisch et al. |
| 2002/0198439 A1 | 12/2002 | Mizuno |
| 2003/0018280 A1 | 1/2003 | Lewkowicz et al. |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0214579 A1 | 11/2003 | Iddan |
| 2003/0216622 A1 | 11/2003 | Meron et al. |
| 2004/0027459 A1 | 2/2004 | Segawa et al. |

FOREIGN PATENT DOCUMENTS

| | | |
|---|---|---|
| DE | 34 40 177 | 5/1986 |
| JP | 57-45833 | 3/1982 |

(Continued)

OTHER PUBLICATIONS

"Robots for the future"—Shin–ichi, et al, printed Nov. 29, 2001.

"The Radio Pill", Rowlands, et al., British Communications and Electronics. Aug. 1960, pp. 598–601.

(Continued)

*Primary Examiner*—Beverly M. Flanagan
(74) *Attorney, Agent, or Firm*—Pearl Cohen Zedek Latzer, LLP

(57) ABSTRACT

A sensing device includes a magnetohydrodynamic propulsion system. The sensing device may be an in-vivo autonomous capsule with an imager, but may be another type of sensing device.

18 Claims, 10 Drawing Sheets

FOREIGN PATENT DOCUMENTS

| | | |
|---|---|---|
| JP | HEI3-289779 | 12/1991 |
| JP | 4109927 | 4/1992 |
| JP | HEI4-109927 | 4/1992 |
| JP | 4144533 | 5/1992 |
| JP | HEI4-180736 | 6/1992 |
| JP | 5015515 | 1/1993 |
| JP | 6114037 | 4/1994 |
| JP | 6285044 | 10/1994 |
| JP | 7289504 | 11/1995 |
| JP | 2001137182 | 5/2001 |
| JP | 2001 224551 | 8/2001 |
| JP | 2001224553 | 8/2001 |
| WO | WO 92/21307 | 12/1992 |
| WO | WO 99/30610 | 6/1994 |
| WO | WO 98/11816 | 3/1998 |
| WO | WO 01/08548 | 2/2001 |
| WO | WO 01/50941 | 7/2001 |
| WO | WO 01/65995 | 9/2001 |
| WO | WO 02/067593 | 8/2002 |
| WO | WO 02/080753 | 10/2002 |

OTHER PUBLICATIONS

"Video Camera to "TAKE""—RF System lab, Dec. 25, 2001.

"Wellesley company sends body montiors into space"—Crum, Apr. 1998.

U.S. Appl. No. 10/361,855, filed Feb. 11, 2003, Iddan.

www.rfnorkia.com—NORIKA3, Jan. 1, 2002.

"Wireless transmission of a color television moving image from the stomach using a miniature CCD camera, light source and microwave transmitter" Swain CP, Gong F, Mills TN. Gastrointest Endosc 1997;45:AB40.

BBC News Online—"Pill camera to 'broadcast from the gut'", Feb. 21, 2000, www.news.bbc.co.uk.

www.rfsystemlab.com—Listing on the N.Y stock exchange, printed Dec. 19, 2001.

www.zatang.com, "Magnetohydrodynamic Propulsion System", printed Jan. 20, 2002.

www.physics.ubc.ca "Magnetohydrodynamics and the Lorentz Force Law", Reg Milley, et al., printed Jan. 20, 2002.

Wang, et al., "Integrated Micro–Instrumentation for Dynamic Monitoring of the Gastro–Intestinal Tract", Presented at IEEE Instrumentation and Measurement Technology Conference, May 2002, Anchorage, Ak, USA, www.see.ed.ac.uk/Naa.publications.html.

U.S. Appl. No. 10/166,025, filed Jun. 11, 2001.

* cited by examiner

SELF PROPELLED DEVICE HAVING A MAGNETOHYDRODYNAMIC PROPULSION SYSTEM

PRIOR PROVISIONAL PATENT APPLICATION

The present application claims benefit from prior provisional patent application Ser. No. 60/354,926 filed on 11 Feb. 2002 and entitled "SELF PROPELLED DEVICE HAVING A MAGNETOHYDRODYNAMIC PROPULSION SYSTEM", incorporated herein by reference in its entirety.

FIELD OF THE INVENTION

The present invention relates generally to self propelled devices, and more specifically to devices having magnetohydrodynamic propulsion, for example for medical, industrial and other applications.

BACKGROUND OF THE INVENTION

Devices and methods for performing in-vivo imaging of passages or cavities within a body are known in the art. Such devices may include, inter alia, various endoscopic imaging systems and devices for performing imaging in various internal body cavities. Devices are also known for collecting other in-vivo data, such as temperature or pressure.

Typical in-vivo sensing systems are passive and are passively moved within the gastrointestinal (GI) tract by gravitation and by the peristaltic action.

There is suggested in the art a remote controlled microscale device for use in in vivo medical diagnosis and/or treatment. Such a device may include a transport capsule containing a plurality of components and a propulsion system.

Among the disadvantages of existing such devices is that any parts such as propellers, or the like, which protrude out of the device during the passage of the device through the intestines or other body cavity may increase the probability of puncturing or wounding or otherwise damaging or irritating the intestinal wall, or the walls of the bodily cavity.

Therefore there is a need for a device such as an in-vivo device which includes an improved propulsion system, one less likely to cause damage to a lumen being traversed.

SUMMARY OF THE INVENTION

Embodiments of the present invention may include a sensing device which includes a magnetohydrodynamic propulsion system. The sensing device may be an in-vivo autonomous capsule with an imager, but may be another type of sensing device. A separate propulsion system may be provided which may be attachable to, for example, a sensing device.

BRIEF DESCRIPTION OF THE DRAWINGS

The invention is herein described, by way of example only, with reference to the accompanying drawings, in which like components are designated by like reference numerals, wherein.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

U.S. Pat. No. 5,604,531 to Iddan et al. and International Patent application PCT/IL01/00218, published as International Publication Number WO 01/65995, both incorporated herein by reference in their entirety for all purposes, disclose various embodiments of autonomous imaging devices usable, inter alia, for gastrointestinal imaging. Various embodiments of the present invention may be used with or incorporated within devices such as those described in U.S. Pat. No. 5,604,531 and/or PCT/IL01/00218; however, embodiments of the present invention may be used with or incorporated within devices having other structures and having other functions.

Figure 1A:
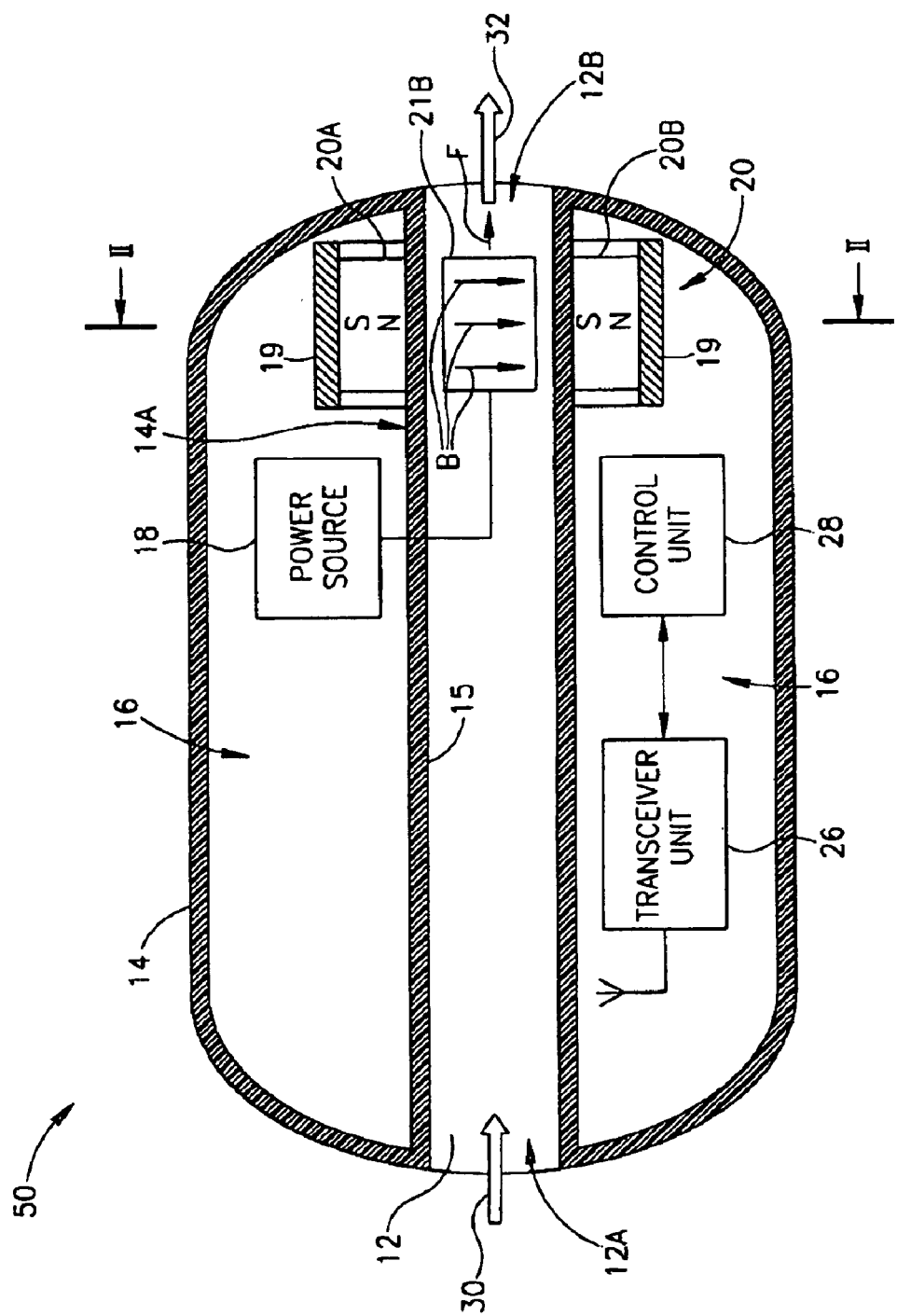
FIG. 1A is a schematic cross-sectional view illustrating a self propelled transport device, using a non-protruding magnetohydrodynamic propelling system, in accordance with an embodiment of the present invention.
Figure 2:
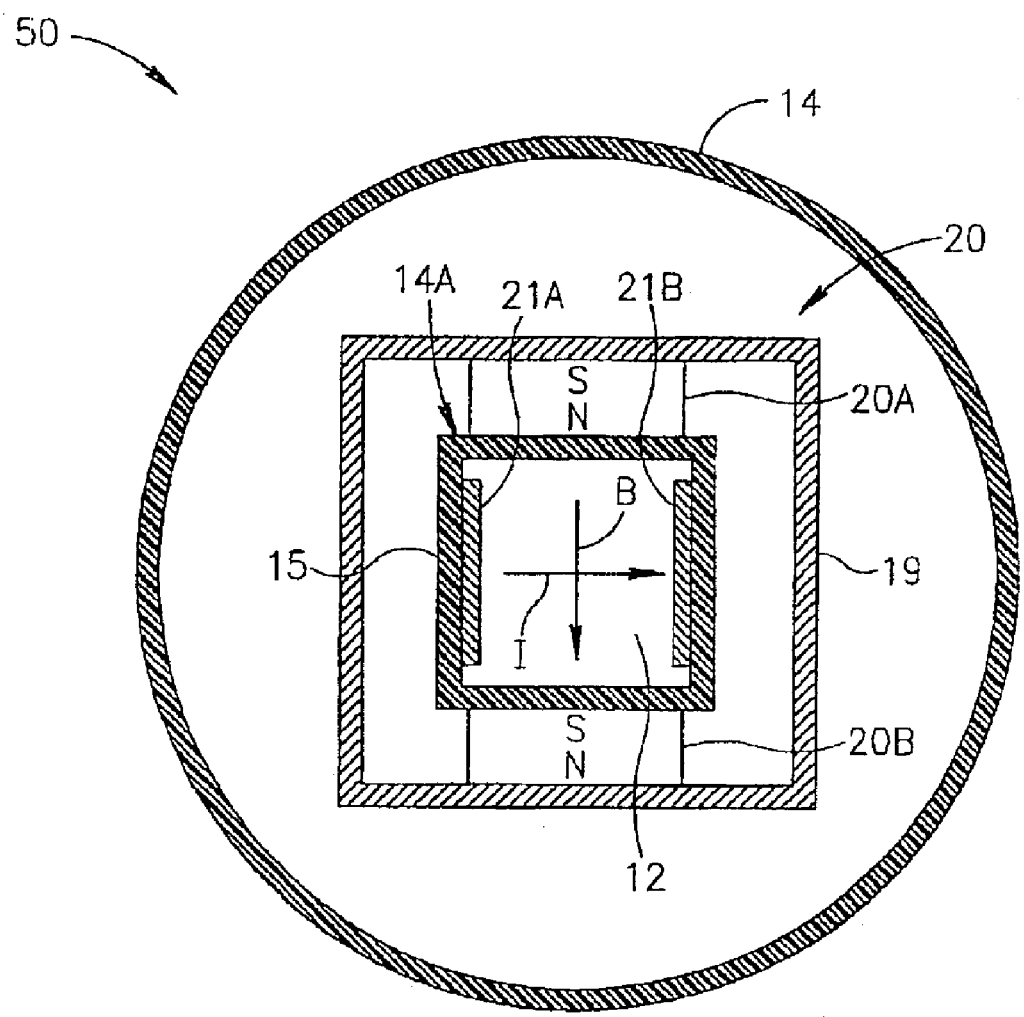
FIG. 2 is a schematic cross-section of the device of FIG. 1A, taken along the lines II—II, in accordance with an embodiment of the present invention.

Reference is now made to FIGS. 1A and 2. FIG. 1A is a schematic cross-sectional view illustrating a self propelled transport device, using a non-protruding magnetohydrodynamic (MHD) propelling system, in accordance with an embodiment of the present invention. FIG. 2 is a schematic cross-section of the device of FIG. 1A, taken along the lines II—II, according to one embodiment.

The transport device 50 may have a body shaped as for example a capsule or elongated member. Such a capsule is typically autonomous and may be ingestible. Other suitable shapes and sizes, such as spherical, ellipsoid, etc., may be used, depending on the application. A hollow duct 12 passes through, typically the length of the device 50. The duct 12 has an opening 12A at a first end thereof and an opening 12B at a second end thereof. The duct may have other configurations and orientations within the device (e.g., the duct need not pass lengthwise) and may have other numbers of inlets or outlets. Further, the reversal of the propulsion system may reverse which ducts are inlets and which are outlets. The duct 12 is typically within or substantially within the device, but need not be. The duct 12 typically accepts fluid and is expels the fluid outward, propelling the device 50.

The walls 14 of the transport device 50 typically enclose an internal space or volume 16 within which various different components (not shown) suitable for performing, for example diagnostic, and/or imaging, and/or therapeutic functions, and/or controlling functions, and/or communication functions may be disposed. Internal space or volume 16 is typically separate from the duct(s) 12. Walls 14 and other structures may define the body or structure of device 50.

The transport device 50 is a general type of transport device and may be used to transport various different such components therewithin. The transport device 50 also includes a magnetohydrodynamic (MHD) propulsion unit 20. The MHD propulsion unit 20 may include a pair (or other numbers) of permanent magnets 20A and 20B. The magnets 20A and 20B are typically attached to the surface 14A of the walls 15 of the duct 12, but may be otherwise attached. Walls 15 and walls 14 may be part of the same structure; one set of walls may be used (when used herein set can include one unit). The north pole of the permanent magnets 20A and 20B is labeled N, and the south pole of the permanent magnets 20A and 20B is labeled S. The arrows labeled B schematically indicate the approximate orientation of the magnetic field between the magnets 20A and 20B, according to one embodiment; other orientations may be used. The permanent magnets 20A and 20B may include suitably permanently magnetized material such as but not limited to suitable Neodymium-iron-boron alloys (NdFeB), samarium-cobalt alloys, or the like. However, any suitable magnets known in the art may be used, provided they generate a sufficiently strong magnetic field.

The permanent magnets 20A and 20B may be (optionally) suitably attached to, for example, a yoke 19. The yoke 19 may be made from (or may include), for example, soft iron, iron, Nickel-iron alloys, or the like. However, other suitable materials which have high magnetic permeability may also be used as is known in the art. The yoke 19 (if used) may increase the strength of the magnetic field B obtained between the magnets 20A and 20B by closing the path of the magnetic flux lines, as is known in the art.

It is noted that while the permanent magnets 20A and 20B are illustrated as having a rectangular prism shape, other different magnet shapes and magnet configurations, and numbers of magnets, may be used. Similarly, while the duct 12 of FIGS. 1 and 2 has a square cross section, the duct 12 may also be shaped to have any other suitable cross section, such as but not limited to, circular, rectangular, ellipsoidal, or other cross sections.

The MHD propulsion unit 20 may further include one or more electrodes 21A and 21B. The electrodes 21A and 21B may be made from a suitable electrically conducting material or materials, such as, for example, electrically conducting metals or alloys, such as but not limited to gold, copper, silver, or the like, gold plated copper, or any other suitable electrically conducting materials or composite materials, including but not limited to graphite, carbon, or the like.

In a typical embodiment, the propulsion system is substantially or entirely within the device. Thus it is less likely that a moving part will come in contact with, for example, a lumen wall. In alternate embodiments, other configurations for the propulsion unit may be used, using other sets of components.

The device 50 also includes a power source 18 which may be disposed within the volume 16. The power source 18 may be suitably connected to the electrodes 21A and 21B of the MHD propulsion unit 20 by suitable electrical conductors (the electrical conductors are not shown for the sake of clarity of illustration) for providing electrical power to the MHD propulsion unit 20.

In operation, the device 50 may be immersed in an electrically conducting fluid (not shown) which may penetrate the duct 12 and come in contact with the electrodes 21A and 21B. The fluid within the duct 12 may be an aqueous salt solution, or other electrolyte solution in the case of devices usable within chemical reactors or within industrial or household tubing or pipelines, or may be the electrically conducting gastrointestinal fluid present within the gastrointestinal tract for devices which are used for in vivo imaging, or the like.

When an electrically conducting fluid is disposed in contact with the to the electrodes 21A and 21B and the power source 18 is suitably connected to the electrodes 21A and 21B, an electric current I (schematically represented by the arrow labeled I of FIG. 2) flows between the electrodes 21A and 21B. Within the electrically conducting fluid the current may be carried by suitable ions present in the fluid. For example, if the fluid is a solution of sodium chloride (NaCl) in water, positively charged sodium ions ($Na^+$) ions may move towards the cathode (the negatively charged electrode) and negatively charged chloride ions ($Cl^-$) ions may move towards the anode (the positively charged electrode) in a direction opposite to the direction of movement of the sodium ions.

According to the Lorentz force law, when an electrically charged particle such as (but not limited to) an ion moves in a magnetic field in a direction perpendicular to the direction of the magnetic field, a force F will act on the ion in a direction orthogonal to the direction of the magnetic field B and to the direction of the electrical current I (for a negatively charged ion, the direction of movement of the ion is the direction of flow of the electrical current I).

Since the directions of movement of the positively and negatively charged ions between the electrodes 21A and 21B are opposite to each other, the forces acting on the negatively charged and positively charged ions will have the same direction. For example, the direction of the force acting on negatively charged and on positively ions disposed between the electrodes 21A and 21B when the electrode 21B is the positive electrode (the anode) and the electrode 21A (see FIG. 2) is the negative electrode (the cathode), and when the direction of the magnetic field is represented by the arrow labeled B (FIG. 1A) is illustrated by the arrow labeled F of FIG. 1A.

The force F acting on the individual ions within the fluid disposed between the electrodes 21A and 21B propels the fluid in the direction represented by the arrow labeled 32 (FIG. 1A). The MHD propulsion unit therefore ejects a fluid jet in the direction represented by the arrow labeled 32. As a result of the ejection of the fluid jet (not shown), the device 50 may move in the direction opposite to the direction of the arrow 32.

The power source 18 may be any suitable power source for providing electrical power to the MHD propulsion unit 20. For example, the power source 18 may be but is not limited to, one or more batteries, a rechargeable battery(ies), an electrochemical cell, a fuel cell, or any other suitable electrical power source. The power source 18 may also be a power generating unit such as any device suitable for wirelessly receiving power from an external source and for providing electrical power to the MHD propulsion unit 20.

It is noted that in the cases where the power source 18 is a power generating unit for receiving energy from an external source, the power source 18 may include therein, or may be connected to a suitable power storage unit (not shown) for storing the generated energy. The power storage unit may be any suitable storage unit, such as a rechargeable battery, or a super-capacitor storage unit, or the like, as is known in the art.

Thus, the power source 18 may also be a device adapted to wirelessly receive energy from an external energy source, such as, for example by receiving electromagnetic waves from an external transmitter and/or receiver and converting and storing electrical energy for use by the MHD propulsion unit 20 or by any other devices or components included within the transporting device 50.

The power source 18 may receive power from external ultrasonic power sources, or electromagnetic wave sources, or magnetic sources, as is known in the art. The structure and operation of such power sources is well known in the art.

Published International Application number PCT/IL02/00283, publication number WO02/080753, assigned to the common assignee of the present application and incorporated by reference herein in its entirety, discloses methods and systems for transmitting power to an internal device; such methods may be used with embodiments of the present invention. For example, in various embodiments of the present invention, power may be received by the device 50 using, for example, a magnetic field. An energy receiving unit in the device 50 may include a coil configured to receive electromagnetic energy and an element, coupled to the coil, configured for converting the received electromagnetic energy to energy for powering the components of the device. The energy receiving unit may further be configured for storing the voltage, such as by including a capacitor or chargeable battery.

The device 50 may further include a control unit 28 suitably connected to the MHD propulsion unit 20 for controlling the operation of the MHD propulsion unit 20. The control unit 28 may be any suitable type of control unit known in the art. Typically, the control unit 28 may be a micro-controller or microprocessor, as is known in the art, but other types of analog, or digital, or analog/digital hybrid control units may be used. The control unit 28 may include or be combined with a wireless transceiver (or transmitter, or receiver) unit 26, for communicating with an external transmitter and/or receiver unit (an example of which is described below), and for receiving data and/or control commands from the external transmitter and/or receiver.

In operation, the device 50 may be immersed in an electrically conducting fluid or liquid (not shown). For example, in gastrointestinal application the device 50 may be immersed in the fluids present in the gastrointestinal tract. The control unit 28 may apply a voltage difference between the electrodes 21A of the MHD propulsion unit 20 with a certain polarity and magnitude, some of the fluid (not shown) between the electrodes 21A and 21B is propelled or ejected through the opening 12B in the general direction indicated by the arrow 32. The ejecting of the fluid jet through the opening 12B in the direction of the arrow 32 may propel the device 50 in the direction opposite the direction of the arrow 32.

It is noted that the direction in which the device 50 is propelled may be changed by, for example, reversing the polarity of the electrical voltage difference applied between the electrodes 21A and 21B of the MHD propulsion unit 20. In such a case, the direction of the force acting on the charged ions within the fluid is reversed and is opposite from the direction represented by the arrow labeled F the fluid jet may then be ejected from the opening 12A and the device 50 may be propelled in the general direction of the arrow 32.

Such reversing of the polarity of the voltage difference may be controllably performed by the control unit 28 upon receiving (e.g., wirelessly or by wire) an appropriate control command or by any other suitable logic command or any other suitable digital or analog control signal or internally generated logic command.

Figure 1B:
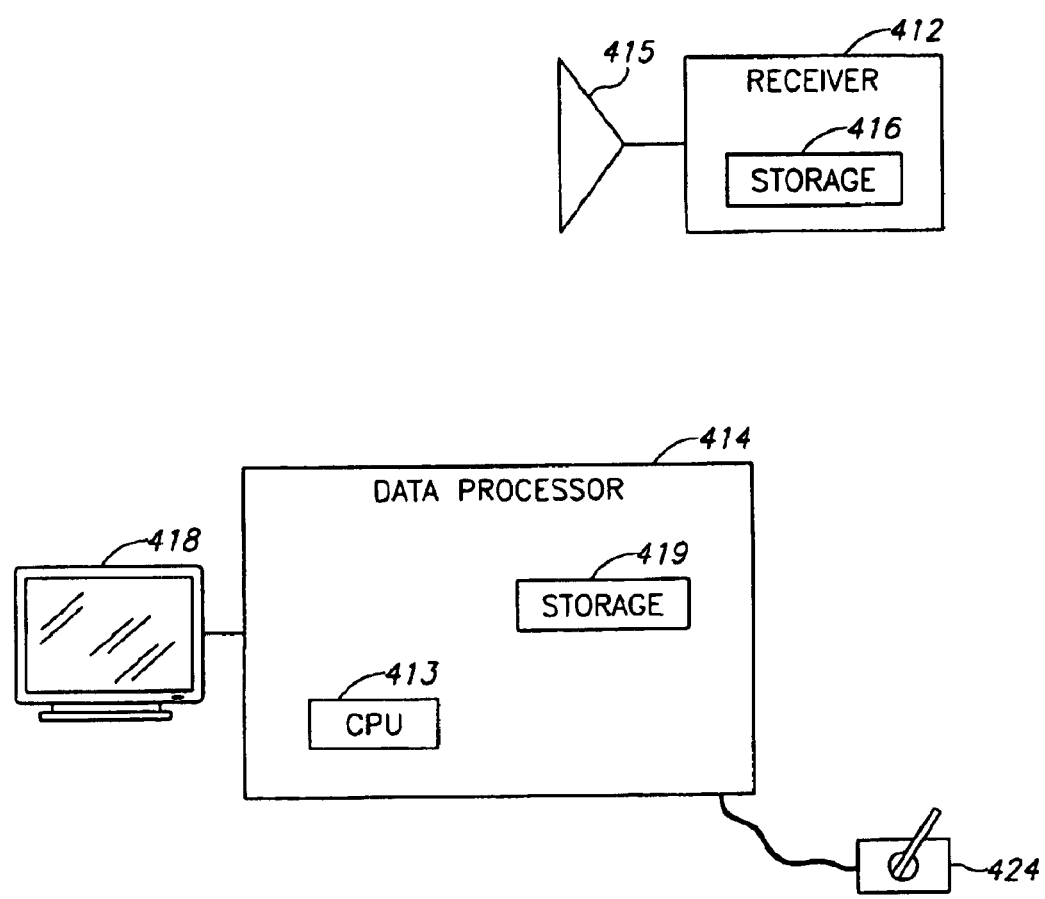
FIG. 1B is a schematic diagram of an external transmitter and/or receiver system and processing system, in accordance with an embodiment of the present invention.

FIG. 1B is a schematic diagram of an external transmitter and/or receiver system and processing system, in accordance with an embodiment of the present invention. Referring to FIG. 1B, preferably, located outside the patient's body in one or more locations, are a transceiver and/or receiver unit 412, preferably including an antenna or antenna array 415, for transmitting data to and/or receiving data from device 50 (FIG. 1A), a receiver storage unit 416, for storing data, a data processor 414, a data processor storage unit 419, and an image monitor 418. In some embodiments image monitor 418 may, for example, display, inter alia, data such as temperature or an image or representation of an in-vivo lumen, transmitted by the device 50 and recorded by the transceiver and/or receiver unit 412. The transceiver and/or receiver unit 412 may, for example, transmit control information or power to the device 50, and may receive image information, location information, temperature information, or other sensor information.

Typically, the transceiver and/or receiver unit 412 and receiver storage unit 416 are small and portable, and are worn on the patient's body during recording of the data. Preferably, data processor 414, data processor storage unit 419 and monitor 418 are part of a personal computer or workstation, which includes standard components such as a processor 413, a memory (e.g., storage 419, or other memory), software, a disk drive, and input-output devices, although alternate configurations are possible. A user control or input system such as a joystick or handle 424, for controlling the movement of the device 50, may be included. Other movement controls may be included, such as, a keyboard, rotating knob, etc, may be used.

In alternate embodiments, the data reception and storage components may be of another configuration. For example, a portable recorder separate from a main workstation or data processor need not be used.

The receiving, recording and processing components may be, for example, similar to embodiments described in U.S. Pat. No. 5,604,531 and/or WO 01/65995. However, the receiving and recording components may be of other configurations.

Figure 3:
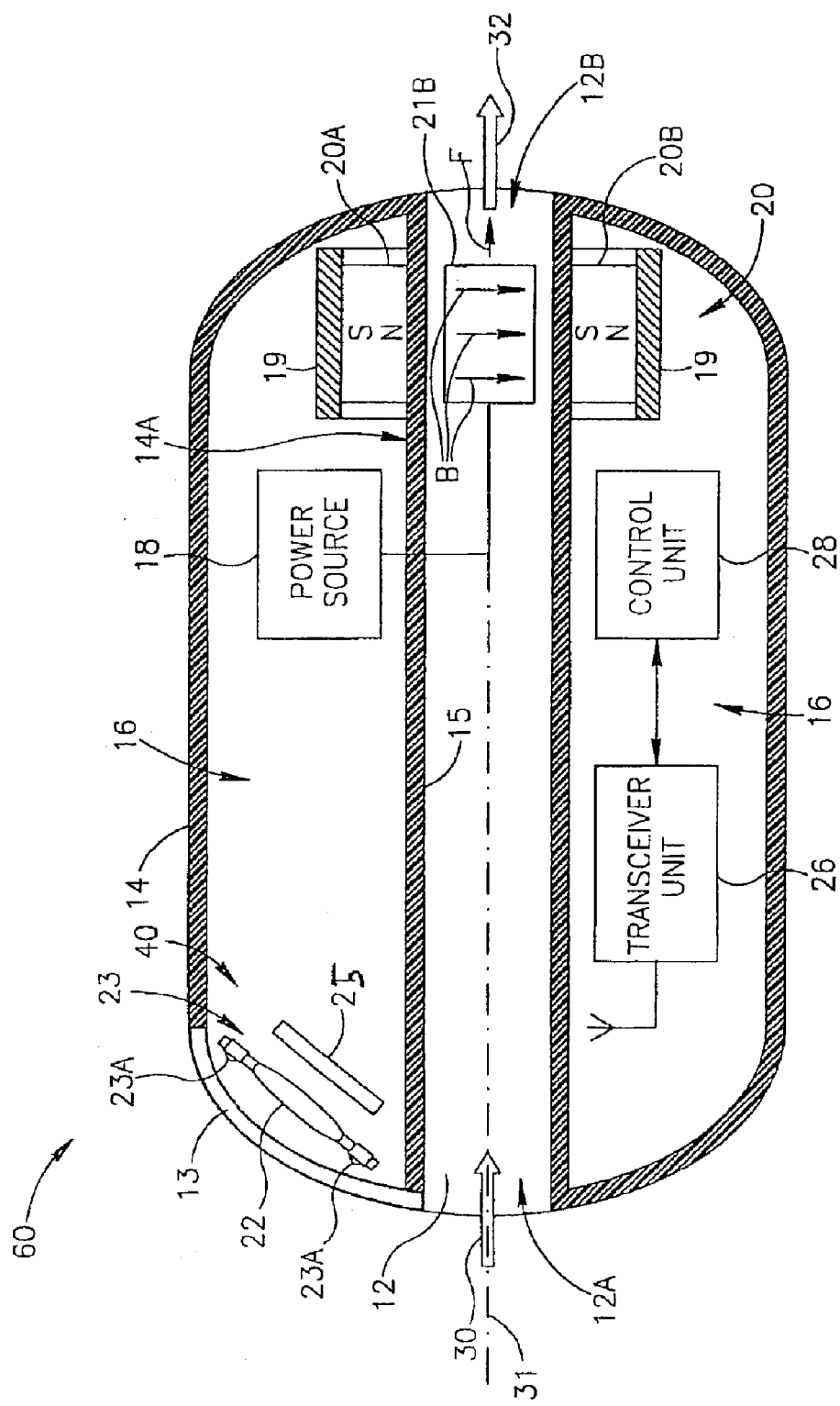
FIG. 3 is a schematic cross-sectional view illustrating a self propelling device including an imaging system, in accordance with an embodiment of the present invention.

Reference is now made to FIG. 3 which is a schematic cross-sectional view illustrating an imaging device using a non-protruding magnetohydrodynamic propelling system, in accordance with an embodiment of the present invention.

The imaging device 60 may include some or all components of the transport device 50 of FIG. 1A and an imaging system 40. Other sensors or sensing systems, such as an ultrasonic sensing system, a pressure sensing system, etc., may be used. The imaging system 40 includes an optical system 22 and an imaging camera 25 (such as a CMOS camera, a CCD camera, or another suitable imaging device) and an illumination unit 23 including one or more of light sources 23A. The optical system 22, the imaging camera 25 and the illumination unit 23, may be constructed and operated as disclosed in detail for the optical system, the imaging camera and the illumination source, of U.S. Pat. No. 5,604, 531 and/or PCT/IL01/00218 (International Publication Number WO 01/65995). However, other imaging systems may be used.

Briefly, the illumination unit 23 may illuminate a target to be imaged (target not shown) on the outside of the device 60 by illuminating the target through an optical window 13 with white light, or infra-red light, or other broadband or narrow-band light, including but not limited to laser light, coherent light, and incoherent light, or any suitable combinations is thereof. The optical window 13 may be made from a material which is transparent to at least some of the wavelengths of light generated by the illumination unit 23 (such as a transparent plastic material, glass, quartz, or the like). An image of the target is focused on the imaging camera 25 by the optical system 22. The illumination unit 23 and the imaging camera 25 are suitably connected to the power source 18 for receiving power therefrom (the connections between the illumination unit 23 and the imaging camera 25 and the power source 18 are not shown for the sake of clarity of illustration). The imaging system 40 is suitably connected to the control unit 28 (the connections between the imaging system 40 and the control unit 28 are not shown for the sake of clarity of illustration).

The control unit 28 may control the operation of, inter alia, the imaging system 40, the illumination unit 23, and the imaging camera 25. In accordance with one embodiment of the present invention, the control unit 28 may be part of or integrated within the imaging camera 25. In accordance with another embodiment, the control unit 28 may be part of or integrated within a wireless transceiver (or transmitter, or receiver) unit.

The control unit may also control the operation and the transmitting and/or (optionally) the receiving of image data and/or command data from an external transceiver or receiver unit, such as that disclosed FIG. 1B. Other external control and/or receiver units may be used.

It is noted that the imaging system 40 may be inclined at an angle to the longitudinal axis 31 of the device 60 as illustrated in FIG. 3. In such a case of a tilted imaging system 40, the target which is imaged is disposed at an angle to the axis 31. It is noted, however, that this tilting is not mandatory and many other optical arrangements are possible, including but not limited to optical arrangements in which the optical system 40 is not inclined at an angle to the axis 31.

It is also noted that while the device 60 has one imaging system 40 therein, other embodiments of the device of the present invention may be made that have more than one imaging systems. In embodiments in which the device includes multiple imaging systems, each imaging system may provide a different image, or the imaging systems may provide images which may be at least partially overlapping. Additionally, in devices having multiple imaging systems, different imaging systems may use different light sources to produce images at different spectral ranges (e.g. images of the same or different targets, using different wavelength ranges). Alternatively, different imaging systems (if used within a single imaging device) may use one or more common light sources, but may acquire images at different wavelength ranges by using appropriate filters, or by using different imager types having different spectral sensitivities.

Figure 4:
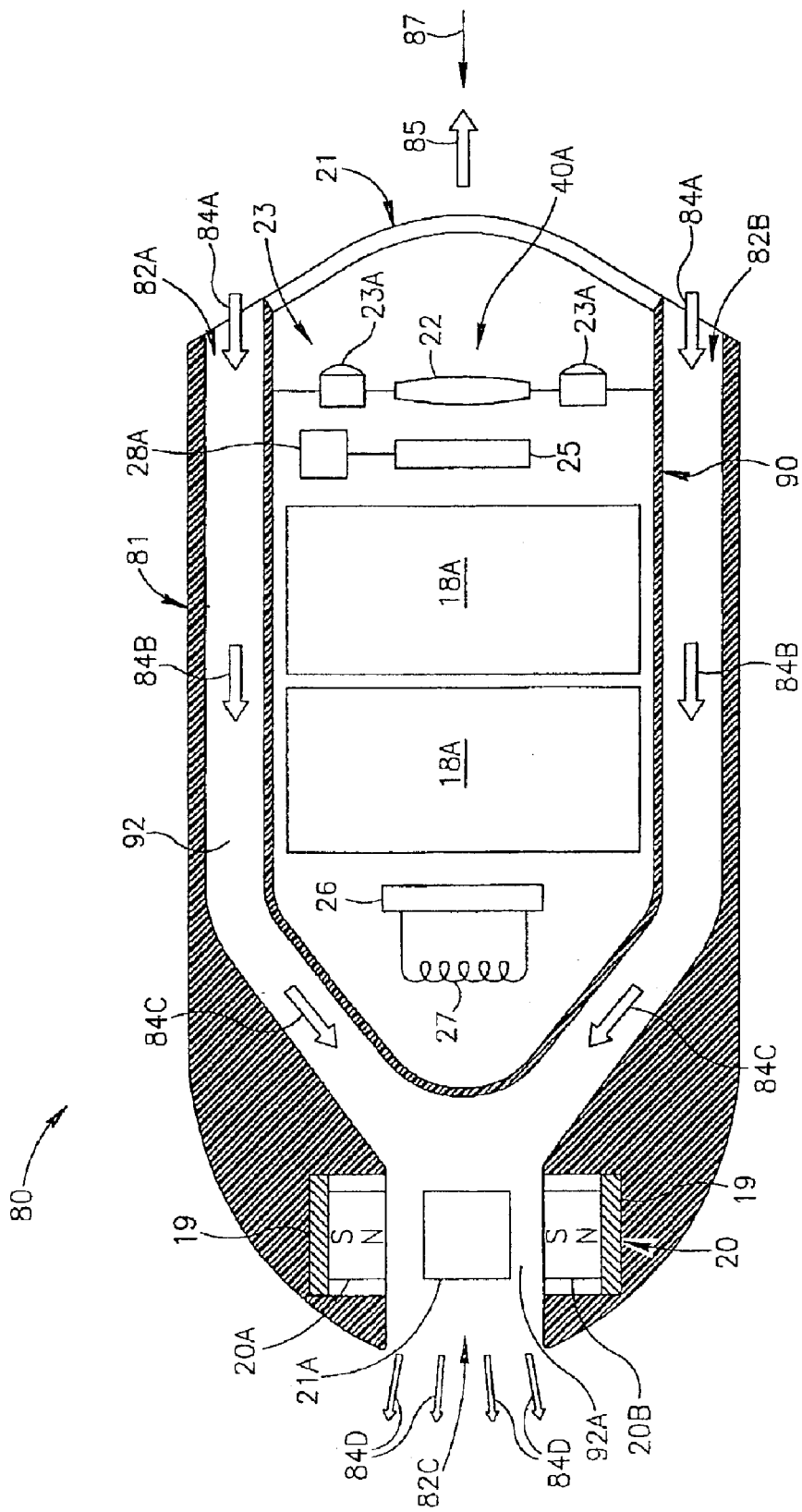
FIG. 4 is a schematic cross-sectional view illustrating an imaging device using a magnetohydrodynamic propelling system, in accordance with an embodiment of the present invention.
Figure 5:
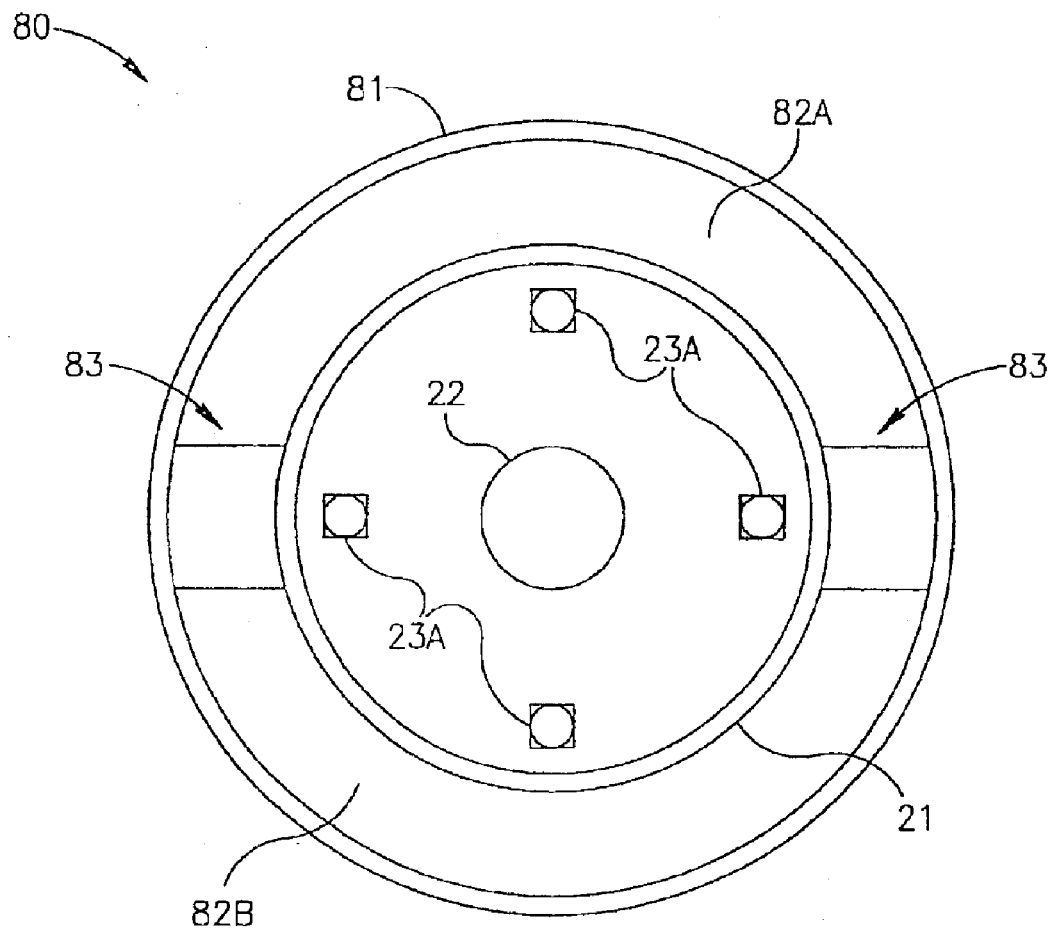
FIG. 5 is a schematic front view of the device illustrated in FIG. 4, in accordance with an embodiment of the present invention.

Reference is now made to FIGS. 4 and 5. FIG. 4 is a schematic cross-sectional view illustrating an imaging device having self propelling capability using another type of non-protruding propelling system, in accordance with an embodiment of the present invention. FIG. 5 is a schematic front view of the device 80 illustrated in FIG. 4, according to one embodiment. The front view of FIG. 5 illustrates the device 80 as seen from the direction represented by the arrow 87.

The device 80 of FIGS. 4 and 5 includes an external housing 81 and an internal housing 90. The internal housing 90 is disposed within the external housing 81 and is attached thereto by attaching members 83 (FIG. 5). The external housing 81 and the internal housing 90 define a hollow duct 92 therebetween. The duct 92 has openings 82A and 82B at one end thereof and an opening 82C at another end thereof. Other duct configurations, other housing configurations, and other numbers of openings may be used. Furthermore, the openings may be placed in other locations, and have other patterns of placement.

The device 80 further includes an MHD propulsion unit 20. The MHD propulsion unit 20 may be similar or identical in structure and operation to the MHD propulsion unit 20 of the devices 50 and 60 as disclosed hereinabove and illustrated in FIGS. 1–3. Some of the components of the MHD propulsion unit 20 such as, for example, the electrodes 21A and 21B (not shown in FIG. 4) may be disposed within the part 92A of the duct 92 and other components of the MHD propulsion unit 20, such as for example the permanent magnets 20A and 20B, and the yoke 19, may be attached to or disposed within or embedded within the walls of the external housing 81 of the device 80, as illustrated in the non limiting exemplary embodiment of FIG. 4.

The device 80 may include a one or more batteries (or electrochemical cells) 18A which may be disposed within the internal housing 90. Other power sources, as discussed herein, may be used. The battery(ies) 18A may be suitably electrically coupled to the MHD propulsion unit 20 by suitable electrically isolated electrical conductors (not shown for the sake of clarity of illustration) for providing power to the MHD propulsion unit 20. Alternatively the application of the voltage difference to the electrodes 21A and 21B may be achieved through the control unit 28A as is known in the art (connections are not shown in detail in FIG. 4).

The imaging device 80 typically includes an imaging system 40A disposed within the internal housing 90. Other sensing systems may be used. The imaging system 40A typically includes an optical system 22 and an imaging camera 25 and an illumination unit 23. The optical system 22, the imaging camera 25 and the illumination unit 23 (which typically includes one or more light sources 23A), may be constructed and operated as disclosed in, for example, U.S. Pat. No. 5,604,531 and/or PCT/IL01/00218 (International Publication Number WO 01/65995). Other imaging systems may be used. The light source(s) 23A may be white light sources, or infra-red (IR) light sources, or other broadband or narrow-band light sources, including but not limited to laser light sources, coherent light sources, and incoherent light sources, or any suitable combinations thereof. Typically, the light sources 23A are light emitting diodes (LEDs), but any other suitable light sources known in the art may be used.

Briefly, the illumination unit 23 illuminates a target to be imaged (target not shown) on the outside of the device 80 by illuminating the target through an optical window 21. The optical window 21 may be made from a material which is transparent to at least some of the wavelengths of light generated by the illumination unit 23 (such as a transparent plastic material, glass, quartz, or the like). An image of the target (not shown) is focused on the imaging camera 25 by the optical system 22. The illumination unit 23 and the imaging camera 25 are suitably connected to the battery(ies) 18A for receiving power therefrom (the connections between the illumination unit 23 and the imaging camera 25, and the battery(ies) 18A are not shown for the sake of clarity of illustration). The imaging system 40A is suitably connected to a control unit 28A which may control the operation of the imaging system 40A.

The control unit 28A may control, inter alia, the operation of the imaging system 40A, the illumination unit 23, and the imaging camera 25. In accordance with one embodiment of the present invention, the control unit 28A may be part of or integrated within the imaging camera 25.

The control unit 28A may be suitably connected to the MHD propulsion unit 20 for controlling the operation of the MHD propulsion unit 20. The control unit 28A may be any suitable type of control unit known in the art. The control unit 28A may be a micro-controller or microprocessor, as is known in the art, but other types of analog, or digital, or analog/digital hybrid control units may be used. The control unit 28A may also be an integral part of the imaging camera 25, as disclosed hereinabove.

The device 80 may also include a wireless transceiver (or transmitter, or receiver) unit 26, or a wireless transmitter unit, for communicating with an external transmitter and/or receiver unit (such as that described herein), and for receiving data and/or control commands from the external transmitter and/or receiver or transceiver. The transceiver unit 26 may be connected to a suitable antenna 27. The control unit 28A may be an integral part of the wireless transceiver (or transmitter, or receiver) unit 26.

In operation, the device 80 may be immersed in a fluid or liquid (not shown). For example, in gastrointestinal application the device 80 may be immersed in the fluids present in the gastrointestinal tract. When electrical power is supplied to the electrodes 21A and 21B of the MHD propulsion unit 20 with a certain polarity as disclosed in detail hereinabove for the MHD propulsion unit 20 of the device 50. The fluid between the electrodes 21A and 21B may then be propelled through the duct 92 in the direction schematically represented by the arrows labeled 84B, and 84C. The fluid may then be forcibly ejected out from the opening 82C as a fluid jet (et not shown) in the general direction indicated by the arrows labeled 84D. The ejecting of the fluid jet through the opening 82C in the direction of the arrows labeled 84D may propel the device 80 in the direction opposite the direction schematically represented by the arrow labeled 85.

It is noted that the direction in which the device 80 is propelled may be changed by reversing the polarity of the electrical current flowing through the electrodes 21A and 21B of the MHD propulsion unit 20 by the batteries 18A. In such a case, the fluid may be taken in through the opening 82C and a fluid jet is ejected from the openings 82A and 82B, and the device 80 may be propelled in the general direction of the arrow labeled 87.

Such reversing may be controllably performed by the control unit 28A upon receiving (e.g., wirelessly or by wire) an appropriate control command or an internally generated logic command or control signal.

It is noted that while the devices 50 and 60 (of FIGS. 1–2 and FIG. 3, respectively) have a single central duct 12 having a first opening 12A and a second opening 12B, and while the device 80 of FIGS. 4–5 has a partially circumferential duct 92 having two openings 82A and 82B and a third opening 82C, many other configurations of the ducts and openings may be used in various different embodiments of the present invention all of which are considered to be within the scope and spirit of the present invention.

For example, in accordance with other embodiments of the invention, any device of the devices 50, 60 and 80 may be modified or configured to include more than one duct. The use of a plurality of ducts may be advantageous since it may be possible to configure the ducts such that their openings may be oriented in different direction. This arrangement may enable the ejection of different fluid jets in different directions (e.g., simultaneously or sequentially) which may improve the ability to control the direction of propelling of the device.

If a device includes a plurality of separate ducts, each duct may (optionally) include a separate MHD propulsion unit (such as, but not limited to the MHD propulsion unit 20 disclosed in detail hereinabove). Such separate MHD propulsion units may be suitably controlled by the control unit operating the device (such as, for example, the control unit 28 or 28A of FIG. 1, and FIG. 4, respectively).

Alternatively, in accordance with another embodiment of the present invention, the device may include a common duct having a single MHD propulsion unit disposed therewithin, such as but not limited to the MHD propulsion unit 20 disclosed hereinabove. The common duct may have one or more openings for fluid intake, and secondary ducts branching thereof. Each of the secondary ducts may have a plurality of openings through which fluid may be ejected to provide a propulsive force or forces. Some or all of the secondary ducts and the openings thereof may be configured such that they are capable of ejecting fluid jets oriented at various different directions relative to the longitudinal axis of the device.

One or more of the secondary ducts may have controllable valves disposed therein and suitably connected to a control unit (such as, but not limited to, the control units 28, and 28A) to control the ejection of the fluid jets through the opening(s) of the secondary ducts. This arrangement may be advantageous since it may provide a more flexible propulsion capability and may be capable of controllably propelling the device in different directions by selectively opening and closing various combinations of valves. Another advantage of this embodiment is that a single MHD propulsion unit may be used while still enabling the control of device propulsion through controlling of appropriately selected valves.

It is further noted that the control units 28 and 28A of the devices 50, 60 and 80 disclosed hereinabove may be used to control the parameters of the fluid jet ejection, such as, inter alia, the fluid jet direction and velocity by controlling the parameters of the current I flowing between the electrodes 21A and 21B of the MHD propulsion unit 20. These current parameters may include, inter alia, the current magnitude, the current's polarity, the current duration and waveform (continuous currents or pulsatile currents may be used). Similar control of these and other current parameters may also be used in embodiments of the invention having multiple MHD propulsion units.

The use of multiple fluid jets having different orientations and velocities may be used to propel the device(s) in various different directions, and to provide not only forward or backward propulsion directions but also various rotational movements (such as for example, a rotation of the device around the longitudinal device axis), and may be used to rotate the device in different directions at an angle to the longitudinal axis of the device. Thus, in principle, movement control methods known in the art for devices based on the ejection of a fluid, or a gas, or a liquid (such as, but not limited to, jet planes rockets, missiles, marine and submarine vehicle propulsion systems, and the like) may be adapted for use in the devices of the present invention.

It is noted that in accordance with other embodiments of the present invention, the devices of the present invention may include more than one MHD propulsion unit. For example, devices including a single or multiple ducts may include a single MHD propulsion unit as illustrated in FIGS. 1 and 4, but may also have multiple MHD propulsion units. These MHD propulsion units may be suitably disposed within suitable ducts in devices which have a plurality of ducts. Alternatively, in devices having a single duct or multiple ducts, more than one MHD propulsion unit may be included in one duct.

In devices having a common duct with secondary ducts, one or more MHD propulsion unit(s) may be included in the common duct, or one or more MHD propulsion unit(s) may be included in some or all of the secondary ducts.

It is noted that the MHD propulsion unit 20 disclosed hereinabove and illustrated in FIGS. 1–5 is only one possible exemplary implementation of the invention and that many variations and modifications of the design of the transport and imaging devices and of the MHD propulsion unit are possible, all of which are considered to be within the scope and spirit of the present invention. For example, while the duct 12 of FIGS. 1–3 is a square duct, many other types of ducts may be used such as but not limited to rectangular, elliptical, circular, and other duct shapes.

Additionally, while in the MHD propulsion unit 20 the magnetic field B is generated by permanent magnets (such as, for example, the permanent magnets 20A and 20B of FIGS. 1–2 ), other devices and methods may be used to generate the magnetic field B. For example, the magnetic field B may be provided by replacing the permanent magnets 20A and 20B with a one or more (in the present example, two) of suitable electrically conducting coils.

Figure 6:
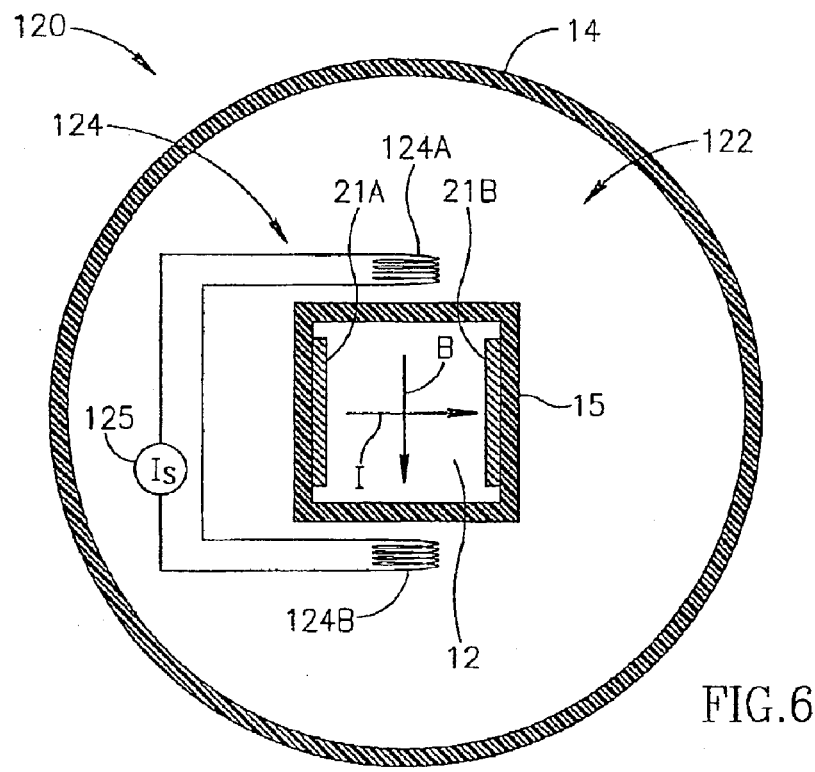
FIGS. 6–8 are schematic cross-sectional views illustrating different exemplary configurations of magnetohydrodynamic propulsion units usable in the devices of the present invention, in accordance with different embodiments of the present invention.
Figure 7:
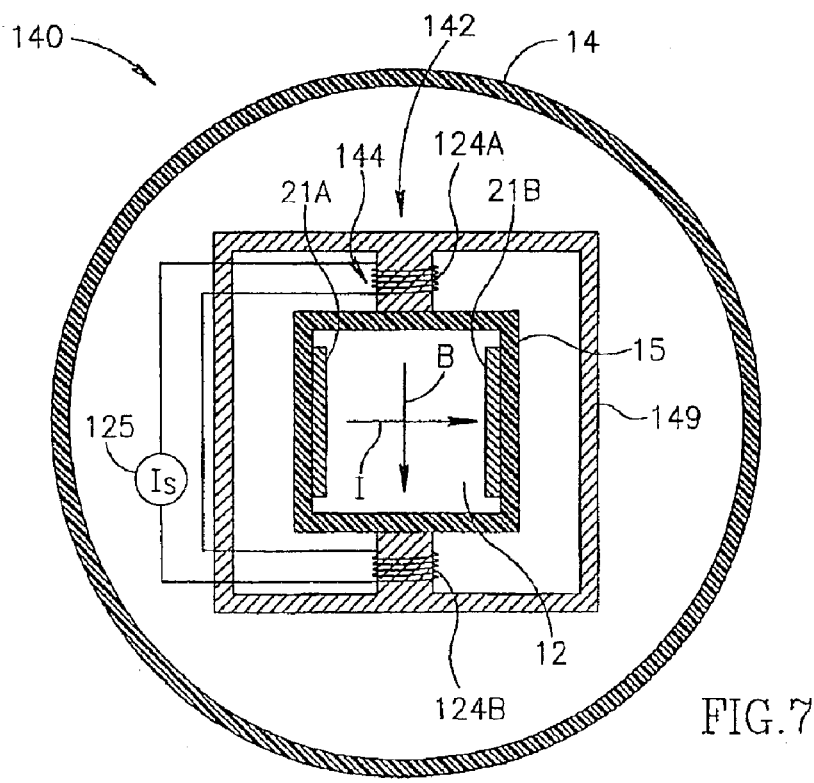
Figure 8:
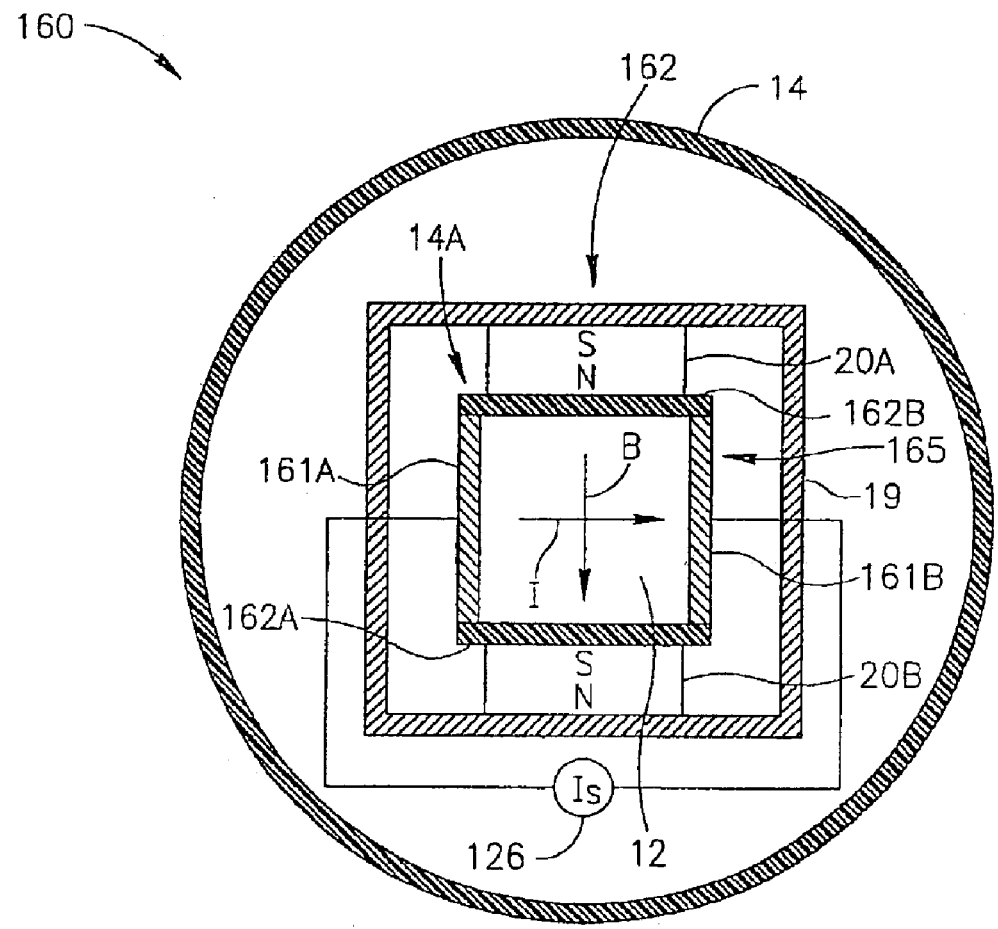

Reference is now made to FIGS. 6–8 which are schematic cross-sectional views illustrating different exemplary configurations of magnetohydrodynamic propulsion units usable in the devices of the present invention, in accordance with different embodiments of the present invention.

FIG. 6 illustrates (in a cross-sectional view) a configuration of an MHD propulsion unit 122 (included in a device 120) utilizing a magnetic field B generated by an electromagnet 124. The electromagnet 124 may include two complementary electrically conducting coils 124A and 124B. The electromagnet 124 may be energized by a current source 125. The current source 125 may be any suitable current source known in the art including but not limited to any of the power sources 18, 18A and 118 disclosed hereinabove. The current source 125 may be a direct current source, an alternating current source, a variable current source, a pulsatile current source, or any other suitable controllable or switchable current source known in the art. A current flowing through the coils 124A and 124B may produce a magnetic field B directed in the approximate direction represented by the arrow labeled B. It is, however, noted that the direction of the magnetic field B may be reversed by reversing the direction of the current flowing through the coils 124A and 124B.

The parameters of the current generated by the current source 125 (or by any other additional source which may optionally be coupled to the electrodes 21A and 21B) may be controlled by a suitable controller unit (not shown in FIG. 6) such as but not limited to the control units 28, 28A and the controller/processor 28B disclosed herein and illustrated in FIGS. 1, 3, 4, and 9. Such parameters may include, inter alia, the current amplitude, the current polarity, and the current waveform. The current may be direct current or may be any suitable time varying or pulsatile current waveform known in the art. The duct 12 the walls 14 of the device 120, and the electrodes 21A and 21B, may be constructed and operated as described in detail for MHD unit 20 of the device 50 (FIG. 2). Thus, the parameters of the current flowing through the coils 124A and 124B, and the parameters of the current flowing through the electrodes 21A and 21B, may be (optionally) separately controlled. Separate control of these current may be advantageous for improving the operation of the MHD propulsion unit 122.

It is noted that the electrodes 21A and 21B may be similar to the electrodes 21A and 21B disclosed in detail hereinabove and illustrated in FIG. 2. The electrodes 21A and 21B may be suitably connected to a current source. The current source may be the current source 125 but may also be another separate current source. The electrical conductors connecting the electrodes 21A and 21B to the current source (either the current source 125 or another separate current source) are not shown for the sake of clarity of illustration. A possible (but not obligatory) direction of the current I flowing in the fluid disposed between the electrodes 21A and 21B is shown by the arrow labeled I. The current direction may be reversed as disclosed in detail hereinabove.

FIG. 7 illustrates (in a cross-sectional view) a configuration of an MHD propulsion unit 142 (included in a device 140) utilizing a magnetic field B generated by an electromagnet 144. The electromagnet 144 may include two complementary electrically conducting coils 124A and 124B and an electromagnet yoke 149. The yoke 149 may be made from or may include one or more magnetizable materials, such as but not limited to, iron or any other suitable metal or metal alloy, as is known in the art. The electromagnet 144 may be energized by a current source 125. The current source 125 may be any of the current source types as disclosed in detail hereinabove for the current source 125 of the device 120 of FIG. 6. A current flowing through the coils 124A and 124B may produce a magnetic field B directed in the approximate direction represented by the arrow labeled B. It is, however, noted that the direction of the magnetic field B may be reversed by reversing the direction of the current flowing through the coils 124A and 124B.

The parameters of the current generated by the current source 125 (or by any other additional source which may optionally be coupled to the electrodes 21A and 21B) may be controlled by a suitable controller unit (not shown in FIG. 7) such as but not limited to the control units 28, 28A and the controller/processor 28B disclosed herein and illustrated in FIGS. 1, 3, 4, and 9. Such parameters may include, inter alia, the current amplitude, the current polarity, and the current waveform. The current may be direct current or may be any suitable time varying or pulsatile current waveform known in the art. The duct 12 the walls 14 of the device 120, and the electrodes 21A and 21B, may be constructed and operated as described in detail for MHD unit 20 of the device 50 (FIG. 2). Thus, the parameters of the current flowing through the coils 124A and 124B, and the parameters of the current flowing through the electrodes 21A and 21B, may be (optionally) separately controlled. Separate control of these current may be advantageous for improving the operation of the MHD propulsion unit 122.

It is noted that the electrodes 21A and 21B may be similar to the electrodes 21A and 21B disclosed in detail hereinabove and illustrated in FIG. 2. The electrodes 21A and 21B may be suitably connected to a current source. The current source may be the current source 125 but may also be another separate current source. The electrical conductors connecting the electrodes 21A and 21B to the current source (either the current source 125 or another separate current source), are not shown for the sake of clarity of illustration. A possible (but not obligatory) direction of the current I flowing in the fluid disposed between the electrodes 21A and 21B is shown by the arrow labeled I. The current direction may be reversed as disclosed in detail hereinabove.

FIG. 8 illustrates (in a cross-sectional view) a configuration of an MHD propulsion unit 162 (included in a device 160) utilizing a magnetic field B generated by yoked permanent magnets 20A and 20B. The MHD propulsion unit 162 is similar in operation to the MHD propulsion unit 20 of FIG. 2, except that the electrodes of the MHD propulsion unit 162 are different from the electrodes 21A and 21B of FIG. 2, and the duct 165 of the device 160 is different than the duct 12 of the device 50 of FIG.2.

The duct 165 of the device 160 includes, for example, two (or other numbers of) electrically conducting electrodes 161A and 161B which are parallel to each other and are sealingly attached between a first duct wall 162A and a second duct wall 162B. The first duct wall 162A and the second duct wall 162B may be parallel to each other and may be made from an electrically isolating material, such as but not limited to a suitable plastic, glass, or any other suitable electrically non-conducting material. The electrodes 161A and 161B and the first duct wall 162A and the second duct wall 162B together form the duct 165 or (optionally a portion thereof). The electrodes 161A and 161B may (but need not necessarily) extend the entire length of the duct 165. The electrodes 161A and 161B may be connected to a current source 126 which may be similar to the current source 125 disclosed hereinabove. The current source 126 may force a current I to flow in the fluid (not shown) disposed between the electrodes 161A and 161B in the approximate direction indicated by the arrow labeled I. The current source 126 may be controlled by a control unit (not shown in FIG. 8), such as but not limited to the control units 28, 28A, the controller/processor unit 28B disclosed herein.

It will be appreciated by those skilled in the art that the devices disclosed and illustrated herein are not limited to including only imaging systems. Many other types of different diagnostic, therapeutic, surgical, and sampling devices may be included in the self propelling devices according to embodiments of the present invention.

It is further noted that, while the devices of the present invention may include an imaging system therein, the imaging system is not an obligatory part of the self propelled devices of the present invention and many such self propelled devices with a non-protruding MHD propulsion unit or MHD propelling system may be constructed in accordance with embodiments of the present invention, which do not include an imaging system but which may include any suitable combination of therapeutic, and/or diagnostic, and/or surgical, and/or spectroscopic, and/or sampling, and/or ultrasonic, components known in the art.

Figure 9:
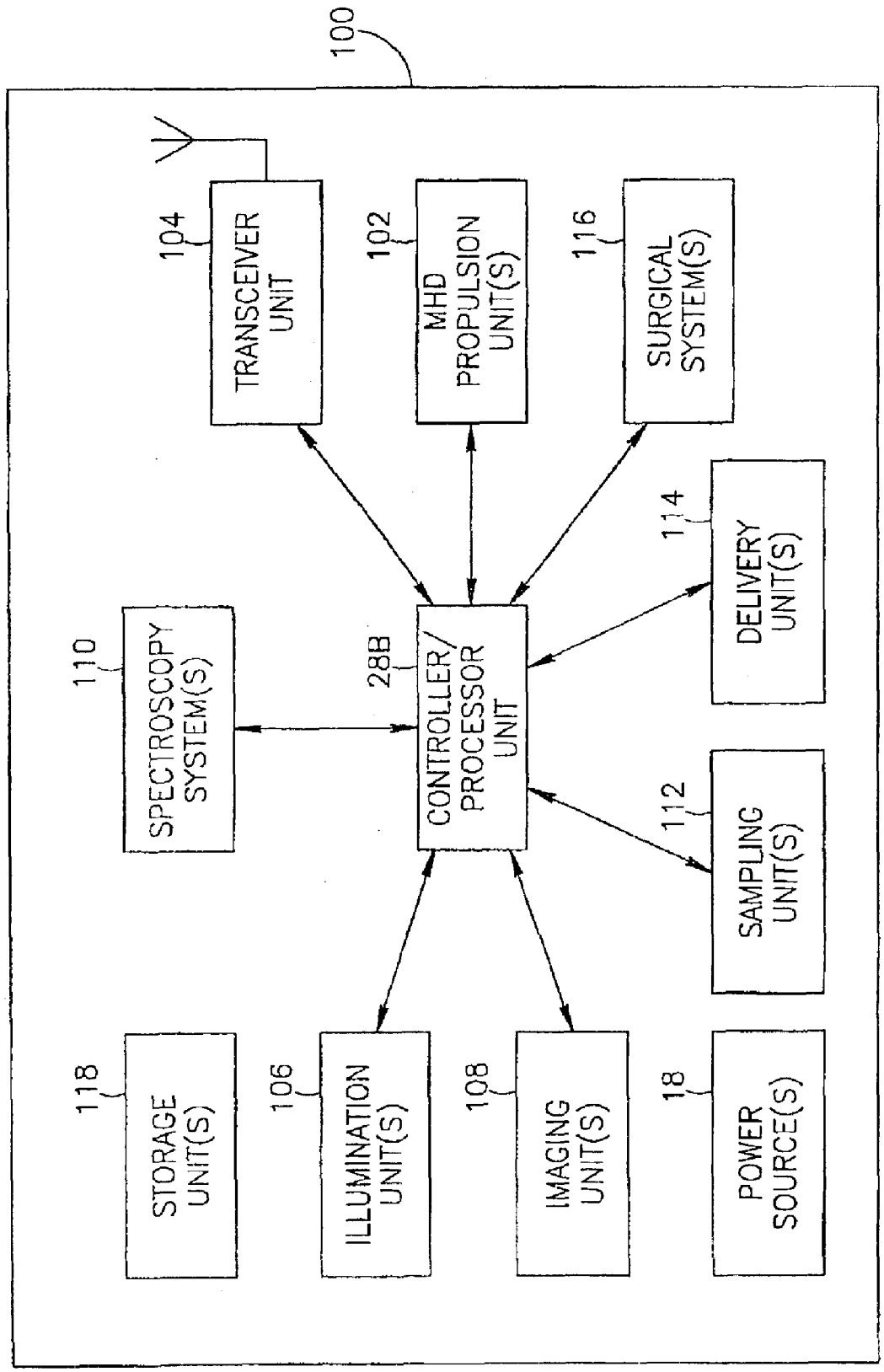
FIG. 9 is a schematic block diagram illustrating the components of an exemplary self propelling imaging/diagnostic/therapeutic device having a non-protruding magnetohydrodynamic propelling system, in accordance with an embodiment of the present invention.

Reference is now made to FIG. 9 which is a schematic block diagram illustrating the components of an exemplary self propelling imaging/diagnostic/therapeutic device having a non-protruding magnetohydrodynamic propelling system, in accordance with another embodiment of the present invention.

The device 100 includes a controller/processor unit 28B, one or more typically non-protruding MHD propulsion units 102, a transceiver unit 104, one or more illumination units 106, one or more imaging units 108, and one or more power sources 18. The controller/processor unit 28B is suitably connected to the propulsion unit(s) 102, the transceiver unit 104, the illumination unit(s) 106, and the imaging unit(s) 108, for controlling the operation thereof.

The device 100 may further include one or more spectroscopy units 110, one or more sampling units 112, one or more delivery units 114, and one or more surgical systems 116. The controller/processor unit 28B may be suitably connected to the spectroscopy unit(s) 110, the sampling unit(s) 112, the delivery unit(s) 114, and the surgical system(s) 116, for controlling the operation thereof.

The spectroscopy unit(s) 110 may be adapted for performing spectroscopic analysis of target tissues (in in vivo applications) or of target objects in other industrial applications, as is known in the art.

The sampling units 112 may be configured and adapted to collect samples of body fluids or to collect a biopsy sample (in in-vivo applications) or to collect samples of other fluids in other industrial applications as is known in the art.

The delivery units 114 may be configured and adapted to deliver quantities of a substance or substances to a target body part or organ part or to a body lumen (in in-vivo applications). The substance(s) which may be delivered may be a drug, a therapeutic substance or other medication, or a pharmaceutical composition. Typically, the substance(s) may be delivered in a liquid form which is dispensed from the delivery unit(s) 114 which include a controllably openable storage vessel.

The delivery units 114 may be configured and adapted to deliver quantities of a substance or substances to a target site in other industrial applications, as is known in the art.

The surgical systems 116 may be adapted and configured to perform one or more of surgical procedures, including but not limited to perform a biopsy procedure (typically, but not necessarily, under visual control), resection of a tumor or part thereof, surgical removal of intestinal or other polyps, or the like. Many other surgical procedures may be performed by the surgical systems 116, such as, laser ablation of target tissues, photo-dynamic therapy (PDT) procedures, which may or may not include the delivery of a suitable PDT dye from the delivery unit(s) 114, or any other suitable surgical procedure.

The details of construction and operation of the spectroscopy unit(s) 110, the sampling unit(s) 112, the delivery unit(s) 114, and the surgical system(s) 116, are known in the art. Briefly, the spectroscopy unit(s) 110, the sampling unit(s) 112, the delivery unit(s) 114, and the surgical system(s) 116 may be constructed and operated as is known in the art.

The power source 18 may be suitably connected to, inter alia, the controller/processor unit 28B, the propulsion unit(s) 102, the transceiver unit 104, the illumination unit(s) 106, the imaging unit(s) 108, the spectroscopy unit(s) 110, the sampling unit(s) 112, the delivery unit(s) 114, and the surgical system(s) 116 for providing power thereto.

The controller/processor unit 28B may be suitably coupled to one or more storage units 118 for storing data, and/or commands, and/or program code therein. The storage unit(s) 118 may include one or more memory devices, such as but not limited to random access memory (RAM) device(s), read only memory (ROM), programmable read only memory (PROM) device(s), electrically programmable read only memory (EPROM) device(s), erasable electrically programmable read only memory (EEPROM) device(s), flash memory (FEPROM) device(s), or the like, or any suitable combinations of memory devices known in the art. However, the storage unit(s) 118 may be any other suitable storage device or storage means known in the art and suitable for storing data or information, such as but not limited to magnetic storage device(s), magneto-optical storage device(s), optical storage device(s), holographic storage device(s), or the like.

It is noted that the spectroscopy unit(s) 110, the illumination unit(s) 106, the surgical systems(s) 116, may or may not include laser device(s) as is known in the art, and may or may not include other coherent or non-coherent light sources (not shown in detail) for illumination, and/or spectroscopy, and/or therapeutic purposes, depending on the specific configuration of the device 100. White light emitting diodes (LEDs) may be included for illuminating and/or spectroscopy purposes, as is known in the art. Other types of LEDs may be also included, such as, but not limited to, infra-red LEDs, and/or LEDs having a narrow or intermediate spectral bandwidth (such as but not limited to red LEDs, green LEDs, blue LEDs, laser diodes, or the like. Other types of light sources known in the art may or may not be included in the device 100 depending on the application.

The controller/processor unit 28B may be any suitable type of control unit known in the art. The controller/processor unit 28B may be a micro-controller or microprocessor, as is known in the art, but other types of analog, or digital, or analog/digital hybrid control units may be used. The controller/processor unit 28B may also be an integral part of one of the imaging units 108, as disclosed hereinabove. Alternatively, the controller/processor unit 28B may be integrated into any other suitable electronic circuit or integrated circuit of the device 100.

It is noted that the connections between the control unit 28 and other components included within the devices 50 and 60 are not shown in detail and are only illustrated schematically. The exact configuration of the connections between the control unit 28 and these components depends on the specific implementation of the devices 50 and 60, are well known in the art.

It is further noted that the connections between the control units 28A and other components included within the device 80 are not shown in detail and are only illustrated schematically. The exact configuration of the connections between the control units 28A and these components depends on the specific implementation of the device 80, are well known in the art.

It is further yet noted that the connections between the control units 28B and other components included within the device 100 are not shown in detail and are only illustrated schematically. The exact configuration of the connections between the control units 28B and these components depends on the specific implementation of the device 100, are well known in the art.

In one embodiment, a propulsion unit may be a separate unit, and may be capable of attachment or joinder to an in-vivo sensing device, or another type of sensing device. In one embodiment, no redesigning of an existing capsule or other sensing device may be needed to add propulsion capability. Such a propulsion unit may be a stand alone unit with separate components, although in some embodiments some components (e.g., power source, controller etc.) may be shared via, for example, a link.

Figure 10:
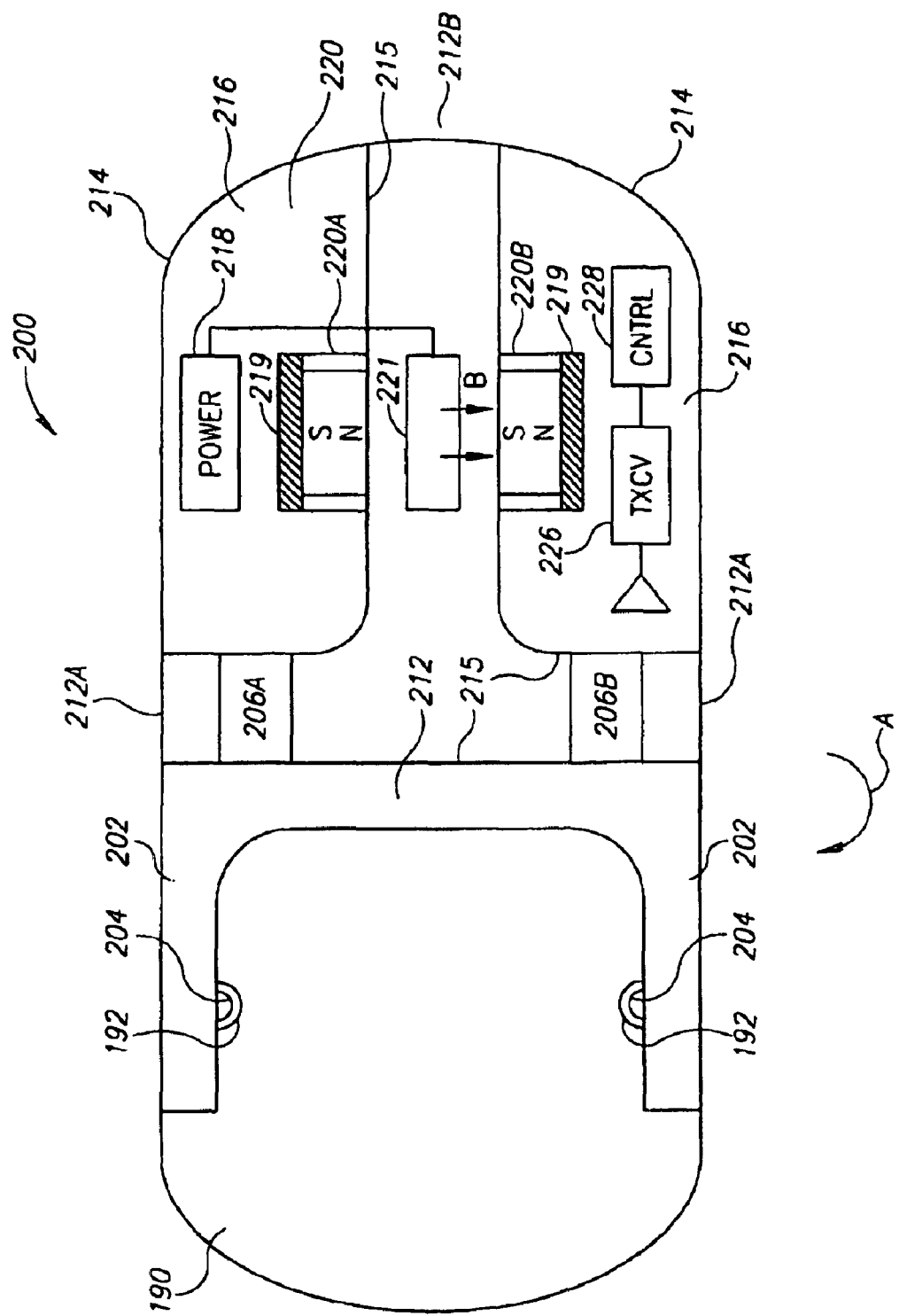
FIG. 10 depicts a propulsion unit connected to an in-vivo sensing device, according to one embodiment of the present invention.

FIG. 10 depicts a propulsion unit connected to an in-vivo sensing device, according to one embodiment of the present invention. Referring to FIG. 10, a propulsion device 200 is connected to an in-vivo sensing device 190. In vivo sensing device 190 may be any sort of in-vivo sensing device, such as those described in U.S. Pat. No. 5,604,531 and/or International Patent application PCT/IL01/00218; other in-vivo sensing devices may be used. In one embodiment, in-vivo sensing device 190 is an oblong capsule, but other shapes (e.g., sphere, ellipse, etc) may be used.

Typically, a connector or connection system such as friction fit sleeve 202 is used to connect propulsion device 200 to sensing device 190. In one embodiment, friction sleeve 202 holds and surrounds a portion of sensing device 190 to propulsion device 200. Sensing device 190 and propulsion device 200 may be separate, autonomous units, and may be connected by a user, at a factory, etc. Typically, when connected, sensing device 190 in combination with propulsion device 200 forms a swallowable shape and size, such as an appropriately sized capsule or sphere, but need not, depending on the application.

In one embodiment, other or additional connectors or connection mechanisms may be used, such as an optional dimple/recess mechanism, where one part, e.g., propulsion device 200, includes one or more dimples or protrusions 204, and another part, e.g. sensing device 190, includes one or more indentations or recesses 192. Other methods of attachment, such as a screw/thread system, etc., may be used.

The components of the propulsion device 200 may be similar in structure and function to those described in the various embodiments above. One or more hollow ducts 212 allow the passage of fluids through body of the propulsion device 200, and include one or more inlets 212A and outlets 212B. The duct(s) 212 is surrounded by the duct walls 215. The walls 214 of the propulsion device 200 enclose one or more cavities or volume(s) 216. Walls 215, walls 214 and/or other structures may define the body of the device 200.

The propulsion device 200 may also include a power source 218, suitably connected to the various components. The power source 218 may be any suitable power source. The propulsion device 200 may include a control unit 228, e.g., a micro-controller or microprocessor, as described above, or another type of control unit. The control unit 228 may be connected to or may include a wireless transceiver unit 226, for external communication, as described above.

The propulsion device 200 includes a magnetohydrodynamic (MHD) propulsion unit 220. The MHD propulsion unit 220 may include a pair (or other numbers) of permanent magnets 220A and 220B. The magnets 220A and 220B are typically attached to the surface 214A of the walls 215 of the duct 212. Walls 215 and walls 214 may be part of the same structure; one set of walls may be used (when used herein set can include one unit). The north pole of the permanent magnets 220A and 220B is labeled N, and the south pole of the permanent magnets 220A and 220B is labeled S. The arrows labeled B schematically indicate the approximate orientation of the magnetic field between the magnets 220A and 220B, according to one embodiment; other orientations may be used. The permanent magnets 20A and 20B may include suitably permanently magnetized material; however, any suitable magnets known in the art may be used.

The permanent magnets 220A and 220B may be (optionally) suitably attached to, for example, a yoke 219.

It is noted that while the permanent magnets 220A and 220B in one embodiment have a rectangular prism shape, other different magnet shapes and magnet configurations, and numbers of magnets, may be used. The duct 212 may have any suitable cross section.

The MHD propulsion unit 220 may further include one or more electrodes 221 (not all electrodes shown for the sake of clarity). The electrodes 221 may be made from a suitable electrically conducting material or materials, such as, for example, electrically conducting metals or alloys, such as but not limited to gold, copper, silver, or the like, gold plated copper, or any other suitable electrically conducting materials or composite materials, including but not limited to graphite, carbon, or the like. The electrodes 221 may be arranged, for example, as shown in the preceding figures.

In a typical embodiment, the propulsion system is substantially or entirely within the device. In alternate embodiments, other configurations for the propulsion unit may be used, using other sets of components.

In one embodiment, in operation, propulsion unit 220 can be activated in a reverse direction, so that fluid flows through the ducts 212 in the opposite direction.

While in one embodiment two peripheral inlets 212A are shown, there can be a ring of any number of openings as well. The propulsion unit 220 unit 224A may be positioned other than in and/or around the central duct of the ducts 212; one or more propulsion units may be in any one of the peripheral channels of the ducts 212. More than one propulsion unit may be used.

In an embodiment where multiple inlets or multiple outlets are used, one or more valves such as selectively operable valves 206 may be used to aid in controlling the direction of movement of the propulsion device 200. Valves 206 may be one-way or two way, adjustable or not, and need not be used or included. For example, in the embodiment shown, the closure of valve 206A while the propulsion unit 220 is reversed may cause the capsule to rotate in the direction of arrow "A". In the embodiment shown, the closure of valve 206A while the propulsion unit 220 is in forward mode may cause the capsule to rotate in the opposite direction of arrow "A". In alternate embodiments, other arrangements of ports may be used. Further, selective flow control can be provided by, for example, more than one propulsion unit. Other components may be used to aid in directing the device. For example, baffles or vanes may alter, increase, decrease or direct the flow of fluid. Rudders may be used.

In one embodiment, a self propelled device as described variously above may be steerable or may otherwise have its direction controlled. In addition, such a device may have its motion or position tracked. Position data may include location and/or orientation data. A position unit or position determining elements may be included within the device (e.g., magnetic coils, a transmitter or antenna) and/or may be external to the device. In one embodiment, location determining elements can be part of the transmitter and/or antenna transmitting other data. Such movement or position information may aid in a user or an automatic system (e.g., an external software program, such as one operating under control of processor 414) in controlling or deciding to operate a propulsion system, or in controlling the direction of movement of such a device.

In one embodiment, location and possibly orientation information for a self-propelled device (such as the devices 50, 60, 80, 100, 190 and/or 200) are determined. Alternately (or in addition), movement information, such as whether or how much the device is moving over time, may be obtained. In one embodiment, motion information may be combined with location and/or orientation information—for example, motion information may provide fine movement determinations not relative to a reference frame. Such information may be used to guide the device, to determine if the device is stuck and needs aid from a propulsion device, or for other reasons. In alternate embodiments, such movement, location and/or orientation information need not be used.

In one embodiment, motion or movement detection may be provided, by, for example, an on-board accelerometer or other device. For example, structures and techniques for motion detection used in International Application No. PCT/IL98/00608, International Publication number WO 99/30610, assigned to the same assignee as the present application, and incorporated by reference in its entirety, may be used.

In a typical embodiment, location detection methods such as those discussed in U.S. Pat. application publication No. US-2002-0,173,718-A1, filed May 20, 2002, entitled "Array System and Method For Locating an In-Vivo Signal Source," assigned to the assignee of the present invention, and incorporated herein by reference, may be used.

Other location and/or orientation detection methods may be used. In one embodiment, the orientation information includes three Euler angles or quaternion parameters; other orientation information may be used. Location and orientation information may be determined by, for example, including two or more transmitting antennas in the above devices, each with a different wavelength, or by detecting the location and orientation using a magnetic method. Methods such as those using ultrasound transceivers or monitors that include, for example, three magnetic coils that receive and transmit positional signals relative to an external constant magnetic field may be used. A GPS or GPS like system may be used; for example a system using transmission from 3 or more stations. If a phase and frequency is used which is high enough (e.g., 300 MHz), a resolution of 1 mm is possible. Other GPS or GPS like systems may be used.

In one embodiment, a transceiver within the device includes, for example, three electrodes, coils or transponders that receive signals (e.g., electromagnetic signals) transmitted from an external source. The external source includes, for example, three transmitters (e.g., electromagnetic transmitters) at a fixed position in an external reference frame that transmit, for example, three distinguishable electromagnetic radiations (such as at different frequencies). The electrodes, coils or transponders receive signals corresponding to the different electromagnetic radiations at a plurality of times, each of the signals including components of at least one of the different radiations. The position of the device can be determined from the data received from electrodes, coils or transponders. The electrodes, coils or transponders form signals that include the components of the signal received by the each electrode from the three transmitters.

Calculations for determining the in vivo position of objects may be carried out on suitable computational or processing devices, for example using data processor 414 and the appropriate software. Such calculations may be any of those known methods described above. For example, data which may aid in location and/or orientation determination is transmitted via, for example, transceiver and/or transmitter unit 26 (described above), received by transceiver and/or receiver unit 412, and downloaded to data processor 414. Alternately, processing capability within the device can determine a position within the reference frame, and this position information may be transmitted via transceiver and/or transmitter unit 26 to be downloaded to data processor 414.

Of course, other location and/or orientation determining methods may be used.

In one embodiment, the data processor 414 displays on monitor 418 a location or path representation of the device. Since the monitor 418 is typically two dimensional, and the path of the device is typically three dimensional, the path representation may be two dimensional, or may be displayed using techniques that include three dimensional information to the two dimensional image. For example, shading or coloring may indicate three dimensional aspects; other techniques may be used. Orientation information may be included. Other methods for displaying location and/or orientation information may be used.

A user may, using a user control or input device (e.g., joystick or handle 424), input information to the data processor 414. The data processor 414 may convert such information into movement controls to be sent to the various components of the device (e.g. the propulsion unit 220, valves, etc.) via transceiver and/or receiver unit 412. For example, commands sent may cause the propulsion unit 220 to alter its speed or reverse its direction. Control information sent to various components may included, for example, information controlling the parameters of the current flowing between the electrodes.

Self propulsion may be desirable for an in-vivo sensing device for various reasons. In one embodiment, where a device traverses the GI tract, propulsion may be desirable in voluminous lumens, such as the stomach or the colon. In the colon, for example, peristaltic motion may be substantially reduced, and thus the device may not be pushed through the colon in an acceptable time frame. The device may stay in the colon until there is bowel movement. The colon typically has a wavy wall structure, and a device may become stuck in one of the waves. Further, at the entrance to the colon (from the small bowel) in the cecum, a device may also get stuck. In addition, the path of an advancing device in the colon may work against gravity, due to the general "C" shape of the colon. In other applications, there may be similar or other reasons why self propulsion is desirable.

Moreover, while the devices 50, 60, 80, 100, 190 and/or 200 are particularly adapted for application as a device for performing imaging and/or therapy/surgery/diagnosis/ procedures within the gastrointestinal tract or within any other body lumen (including but not limited to blood vessels, and the heart), other applications of the present invention may also include devices configured for use in other environment such as, but not limited to imaging and performing sampling, and/or analytical, and/or maintenance, and/or various treatment procedures in industrial or other environments, such as, for example, within vessels, tubes or pipelines in industrial equipment, or within buildings, or the like.

Furthermore, while the devices disclosed hereinabove and illustrated in the drawing figures are autonomous self propelling devices, the non-protruding MHD propulsion system of the present invention may also be used and implemented in other endoscopic devices. Thus, in accordance with additional embodiments of the present invention, an endoscope-like device, or catheter-like device, or tethered capsule-like device may be adapted to include a non-protruding propulsion system in which an MHD propulsion unit may be included within one or more non-protruding duct or cavity within the endoscope-like device, or catheter-like device, with the proper modifications (if necessary) of the duct(s) and/or cavities. In operation, the ejection of one or more fluid jets (not shown) from one or more openings of such duct(s) or cavity, by the MHD propulsion unit, may be used to move or propel or stir the endoscope-like device or the catheter-like device, or the tethered capsule-like device, or a part thereof within the body cavity, or lumen, or the space within which such devices are disposed during their operation.

It will be appreciated by those skilled in the art that while certain configurations of MHD propulsion units are disclosed hereinabove and illustrated in the drawings, this is done by way of way of example only, and that many other types and configurations of MHD propulsion units may be used in the devices present invention, as is known in the art.

While the invention has been described with respect to a limited number of embodiments, it will be appreciated that many variations, modifications and other applications of the invention may be made which are within the scope and spirit of the present invention.

What is claimed is:

1. An in-vivo sensing device comprising:
   a sensor;
   a duct disposed substantially within the device; and
   a propulsion device including a magnetohydrodynamic device.
2. The device of claim 1, wherein the sensor includes an imager.
3. The device of claim 1, comprising a magnet disposed within a volume separate from the duct, and wherein the propulsion device includes at least a plurality of electrodes.
4. The device of claim 3, comprising a yoke connected to the magnet.
5. The device of claim 1, comprising a set of valves.
6. The device of claim 1, comprising a receiver.
7. The device of claim 1, comprising a receiver capable of receiving power from a source external to the device.
8. The device of claim 1, comprising a receiver capable of receiving control information.
9. The device of claim 8 comprising a controller, wherein per the control information the controller is capable of operating the magnetohydrodynamic device.
10. The device of claim 1 wherein propulsion is provided by propelling fluid, the device comprising:
    a set of valves; and
    a controller capable of operating the set of valves to provide directional control of fluid flow.
11. The device of claim 1, comprising a power source.
12. The device of claim 1, comprising a position unit.
13. The device of claim 1, comprising a movement detection unit.
14. The device of claim 1, comprising a coil capable of receiving electromagnetic energy.
15. The device of claim 1, wherein the duct includes at least an inlet and an outlet.
16. The device of claim 1, wherein the duct includes a plurality of outlets.
17. The device of claim 1, wherein the device is an ingestible capsule.
18. An in-vivo imaging device comprising:
    an imager;
    a power source;
    a transmitter;
    a duct disposed substantially within the device; and
    a magnetohydrodynamic device.

* * * * *